US012281349B2

United States Patent
Inoue et al.

(10) Patent No.: US 12,281,349 B2
(45) Date of Patent: Apr. 22, 2025

(54) RECOMBINANT VECTOR COMPRISING GENE FOR SYNTHESIZING HIGH MOLECULAR WEIGHT COPOLYMER, TRANSFORMANT AND METHOD FOR PRODUCING POLYMERS USING TRANSFORMANT, RECOMBINANT STRAINS HAVING GENE FOR SYNTHESIZING HIGH MOLECULAR WEIGHT COPOLYMERS IN GENOME AND METHOD FOR PRODUCING POLYMERS USING RECOMBINANT STRAIN

(71) Applicant: FUENCE CO., LTD., Tokyo (JP)

(72) Inventors: Kozo Inoue, Tokyo (JP); K Sudesh Kumar C Kanapathi Pillai, Penang (MY); Manoj Kumar Lakshmanan, Penang (MY); Hua Tiang Tan, Penang (MY)

(73) Assignee: FUENCE CO., LTD., Tokyo (JP)

( * ) Notice: Subject to any disclaimer, the term of this patent is extended or adjusted under 35 U.S.C. 154(b) by 672 days.

(21) Appl. No.: 17/606,022

(22) PCT Filed: Apr. 24, 2020

(86) PCT No.: PCT/JP2020/017812
§ 371 (c)(1),
(2) Date: Oct. 23, 2021

(87) PCT Pub. No.: WO2020/218566
PCT Pub. Date: Oct. 29, 2020

(65) Prior Publication Data
US 2023/0313240 A1 Oct. 5, 2023

(30) Foreign Application Priority Data

Apr. 26, 2019 (JP) ................. 2019-086890

(51) Int. Cl.
*C12P 7/625* (2022.01)
*C12N 9/10* (2006.01)
*C12N 9/88* (2006.01)

(52) U.S. Cl.
CPC ............ *C12P 7/625* (2013.01); *C12N 9/1029* (2013.01); *C12N 9/88* (2013.01); *C12Y 402/01017* (2013.01)

(58) Field of Classification Search
None
See application file for complete search history.

(56) References Cited

U.S. PATENT DOCUMENTS

| 6,593,116 B1 | 7/2003 | Huisman et al. |
| 6,812,013 B2 | 11/2004 | Yano et al. |
| 2004/0146998 A1 | 7/2004 | Yokomizo et al. |
| 2008/0233620 A1 | 9/2008 | Okubo et al. |
| 2012/0088280 A1 | 4/2012 | Pillai et al. |
| 2013/0017583 A1* | 1/2013 | Budde ............ C12N 9/88 435/254.11 |

FOREIGN PATENT DOCUMENTS

| EP | 1626087 A1 | 2/2006 |
| EP | 2896701 A1 | 7/2015 |
| JP | 2002-523050 A | 7/2002 |
| JP | 2013-510572 A | 3/2013 |
| WO | 2014/042076 A1 | 3/2014 |

OTHER PUBLICATIONS

Chica et al. Curr Opin Biotechnol. Aug. 2005; 16(4):378-84. (Year: 2005).*
Singh et al. Curr Protein Pept Sci. 2017, 18, 1-11 (Year: 2017).*
Accession A0A2Z5DZK9. Oct. 10, 2018 (Year: 2018).*
EPO, Extended European Search Report for European Patent Application No. 20794673.2, Jul. 5, 2023.
Foong Choon Pin et al., "A novel and wide substrate specific polyhydroxyalkanoate (PHA) synthase from unculturable bacteria found in mangrove soil", Journal of Polymer Research, Springer Netherlands, Dordrecht, vol. 25, No. 1, pp. 1-9, Dec. 18, 2017.
Database UniProt [Online] 1.2, SubName: Full=Poly(R)—hydroxyalkanoic acid synthase [ECO 0000313 rEMBL AXB72506 1) EC=2 ~ 3 ~ 1 D-[ECO 0000313 rEMBL AXB72506 1) XP002808786, retrieved from EBI accession No. UNIPROT:A0A2Z5DZK9 Database accession No. A0A2Z5DZK9, Dec. 5, 2018.
Database UniProt [Online], SubName: Full=3-alpha,7-alpha, 12-alpha-trihydroxy-5-beta-cholest-24-enoy 1-CoA hydratase [ECO 0000313 r Embl ALC30197 1 ) XP002808785, retrieved from EBI accession No. Uniprot: A0A0M4DW28 Database accession No. A0A0M4DW28, Jan. 16, 2018.
T. Clement, "Sequence of PHA synthase gene from two strains of Rhodospirillum rubrum and in vivo substrate specificity of four PHA synthases across two heterologous expression systems", Applied Microbiology and Biotechnology, vol. 53, No. 4, pp. 420-429, XP055303853, Berlin/Heidelberg ISSN: 0175-7598, DOI: 10.1007/s002530051636, Apr. 1, 2000.

(Continued)

*Primary Examiner* — Christian L Fronda

(57) ABSTRACT

The primary object of the present invention is to provide a polymer synthase gene which is derived from mangrove soil metagenome, and the method for producing the useful copolymer by using this polymer synthase. Another object of the present invention is to provide an enoyl-CoA hydratase gene which is derived from *Streptomyces* sp. CFMR 7, and the method for producing the useful copolymer, P(3HB-co-3HHx) with increasing the composition of 3HHx by the expression of this enoyl-CoA hydratase.
In order to achieve these objects, an isolated polynucleotide encoding for a polypeptide with polymer synthase activity comprising an amino acid sequence set forth in SEQ ID NO: 1 or 3, or an amino acid sequence set forth in SEQ ID NO: 1 or 3 wherein one or more amino acids is replaced, deleted or added are provided.

18 Claims, 5 Drawing Sheets

Specification includes a Sequence Listing.

(56) References Cited

OTHER PUBLICATIONS

Li Yamei et al., Archives of Microbiology, Springer Berlin Heidelbergr Berlin/Heidelbergr, "Biosynthetic and antimicrobial potential of actinobacteria isolated from bulrush rhizospheres habitat in Zhalong Wetland, China", vol. 200, No. 5, pp. 695-705, XP036528280, ISSN: 0302-8933, DOI: 10.1007/S00203-018-1474-6, Jan. 24, 2018.
Database UniProt [Online] 9-13, SubName: Full=3-alpha,7-alpha, 12-alpha-trihydroxy-5-beta-cholest-24-enoy 1-CoA hydratase (ECO 0000313 iEMBL POG49458 1) XP002809583, retrieved from EBI accession No. Uniprot: AOA283YBR2 Database accession No. AOA2S3YBR2, Jul. 18, 2018.
WIPO, International Search Report for International Application No. PCT/JP2020/017812, Jun. 16, 2020.
WIPO, International Preliminary Report on Patentability including Written Opinion for International Application No. PCT JP2020/ 017812, Jun. 16, 2020.
Japan Patent Office, Office Action for Japanese Patent Application No. 2021-516296, Aug. 10, 2021.
"Uncultured bacterium poly(R)-hydroxyalkanoic acid synthase gene, complete cds" [Jul. 17, 2018], retrieved from GenBank [online], accession No. MF431721.1, [retrieved on Jun. 5, 2020], URL:[http://www.ncbi.nlm.nih.gov/nuccore/MF431721.1/], entire text (Japanese Office Action for Japanese Patent Application No. 2021-516296.
"3-alpha, 7-alpha, 12-alpha-trihydroxy-5-beta-cholest-24-enoyl-CoA hydratase |*Streptomyces* sp. CFMR 7]" [Sep. 2, 2015], retrieved from GenBank [online], accession No. ALC30197.1.1, [retrieved on Jun. 5, 2020], URL:[http://www.ncbi.nlm.nih.gov/protein/ALC30197], entire text (Cited in International Search Report and Written Opinion for International Application No. PCT/JP2020/ 017812 (Japanese Office Action for Japanese Patent Application No. 2021-516296.
Sato et al., "Expression and characterization of (R)-specific enoyl coenzyme A hydratases making a channeling route to polyhydroxyalkanoate biosynthesis in Pseudomonas putida", Appl Microbiol Biotechnol (2011), 90 pp. 951-959, DOI 10.1007/s00253-011-3150-5, Feb. 17, 2021, published online.

\* cited by examiner

Fig. 1

SEQ ID NO: 1

MASKDSPGTTGELNGSMFRWMSQINIAAAQIQQANMRAFAQSMELATSAYAPNWGQPVEQVVPADPRFKDEANTERHAA
GLLFQSYLITSQWLMSIALGWQAIDPDLMERCRFWTQQLVDATSPANFAMTNPVVMQEIAPTGSWNLIQSSGWLLKDAQ
SGRLEQVPEDAFEVGKDLAITFGKVVYKSRLIELIQYTPATETVHBIPILVVPPWINSYXVDWRQPKDSLFFYLVDAGF
TLPTISWKRPDETVLDLEWDPYLDLGTLSALRMVKEIBGVEQVRLVGTCLGGIISQVTLAYLAAIGDDAQIRSAIYFTT
HQDFSDAGEISVFISPLPVWFLEWLMKISGSYLDSENLAATFMMLRANDLINMYVVHNILLSQEPASFDLLYWNRDGIR
VFSKVRSFLLPEFFLGWKLKEFEGIQVKGVGIDLGKITTPTYVVTAGRGBIVPWSBAFLVKQIQSSPVKFILSGGGHIA
GVISPPTKSPGFWIREEKRDDADASLAGATKHDGSWWVDWIPWLSERSGPRVKPSTAAGSDEFRPLSDAPGTYVLEK

Fig. 2

SEQ ID NO: 2
ATGGCGTCAAAGGATAGCTTCGGGAAAACAGGTGATTTGTGGTCATCGATGTTCAACTGGATGAGCGGGACGATGACGGC
CGCGGCACAGATTCAGCAGGCTAATATGCGGGCCTTCGCCCAAAGCATGGAACTGGCAACCAGCGCCTATGCCAGGATGT
GGGGTCAGCCCGTCGAACAGGTCGTGCCGGCCGATCGACGCTTCAAGGATGAGGCCTGGACGGAAAACATGGCCGCCGAT
TTGCTCAAACAGAGCTACCTGATCACCAGTCAGTGGCTAATGGAAATCGCCGATGGTTGGCAGGCTATCGATCCCGATCT
GCACGAACGGACCCGCTTCTGGACACAGCAACTCGTCGACGCCACCAGCCCGGCTAACTTCGCCATGACCAACCCGGTGG
TGATGCAAGAGATAGCCCGCACTGGCGGCATGAACCTGATCCAGGGGGCGCAGAATCTATTGAAGGATGCCCAAAGTGGC
CGGCTAACCCAAGTTCCTGAGGATGCCTTTGAGGTAGGTAACGACCTGGCGATCACGCCGGGCAAGGTCGTATATCGCAA
CCGCCTGATTGAGTTGATCCAGTACACGCCGGCCACAGAGACGGTCCATGAAATCCCCATCTTGGTCGTGCCGCCATGGA
TCAATAAGTACTACGTGATGGACATGCAGCCGGAGAATTCGCTGTTCAAGTACCTGGTGGATGCCGGCTTCACCCTGTTC
ACCATCAGCTGGAAAAACCCTGATGAAACAGTTCTTGACCTGGAATGGGACGACTATCTGGATCTGGGCACGCTGGAAGC
GCTGCGAATGGTCAAGGAAATCATGGGTGTCGAGCAGGTGAACCTGGTCGGCTACTGTCTAGGCGGGATCATCTCCCAGG
TAACTTTGGCCTATCTGCGCGCCACTGGAGACGACGCGCAGATAAACAGCGCGACCTATTTCACCACCCACCAGGATTTC
AGCGATGCGGCGAGATCTCGGTCTTCATCAGCCGGCTGGACGTGATGTTCCTGGAATGGTTGATGAAGATCAGCGGCGG
CTACCTGGATGGCCGGAACCTGGCGGCTACCTTCAACATGCTGCGGGCCAATGACCTGCTATGGAATTACGTGGTCCACA
ATTATCTCTTGGGCCAGGAACCGGCGTCCTTTGATCTACTCTACTGGAATAATGACGGCACCAGGGTACCGGGCAAGGTG
CATTCATTCCTGCTGCCGGAATTCTTCCTGGATAACAAACTGAAGGAGCCCGAGGGTATTCAGGTGAAGGGCGTGGGCAT
TGACCTCGGTAAAATCACAACGCCAACCTATGTCGTGACGGCCGACCGGGATCACATCGTGCCCTGGCGGGGCGCATTCT
TGGTGCGCCAGTTGCAGAGCGGGCCGGTGCGCTTCATCTTGAGCGGCGGCGGACATATCGCCGGGGTCATTAGCCCACCC
ACTAAGAACCGCGGCTTTTGGATCAACGAAGAAGAGAAGGATGATGCTGATGCCTGGCTGGCCGGAGCGACCAAGCATGA
CGGTAGTTGGTGGGTAGATTGGATTCCATGGCTCGAGGAGCGCTCGGGAAGAAGGGTGAAGCCACCGACGGCCGCCGGCA
GCGACCGAGTTCAAACCCCTCATGGACGCGCCAGGCACGTACGTTTGGAGAAGTAG

Fig. 3

SEQ ID NO: 3
MPIDARAALAAAPRRAEIAWNHKDVQLYHLGLGAGIPATDPDELRYTLESRLQVLPSFATVAGAGTAAFGGMGADGIDVD
LAAVLHCGQSVRVHRPIPVTGRAVQTSKVAAVYDKGKAAVIVLRTEAHDDEGPLWTNDAQIFVRGEGGFGGERGPADRLA
LPDRAPDRTAERPIREDQALLYRLSGDWNPLHADPAFAKLAGFDRPILHGLCTYGMVLKAVTDTLLDGDVSHIAAYRTRP
AGVVPPGETLRIRMWQVGDGRVQVAVTAAGHDDAPVLADTLVEHS

Fig.4

SEQ ID NO: 4
ATGCCCATCGATGCCCGAGCGGCCCTCGCCGCAGCCCCCCGCCGAGCCGAGATCGCCTGGAACCACAAGGACGTCCAGCT
CTACCACCTGGGCCTCGGCGCGGGGATCCCCGCCACCGACCCGGACGAGCTGCGCTACACCCTGGAGTCCCGGCTCCAGG
TGCTGCCGAGCTTCGCCACCGTCGCGGGCGCCGGGACGGCCGCCTTCGGCGGGATGGGCGCGGACGGGATCGACGTGGAC
CTCGCCGCCGTCCTGCACGGCGGCCAGTCCGTCCGCGTCCACCGCCCGATCCCCGTCACCGGCCGGGCCGTGCAGACCTC
GAAGGTCGCGGCCGTGTACGACAAGGGCAAGGCCGCCGTCATCGTGCTCCGTACCGAGGCGCACGACGATGAGGGGCCGC
TCTGGACCAACGACGCGCAGATCTTCGTACGGGAGAGGGCGGATTCGGCGGCGAGCGCGGGCCCGCCGACCGCCTCGCC
CTGCCCGACCGGGCCCCGACCGCACCGCCGAACGCCCGATCCGCGAGGACCAGGCGCTGCTCTACCGCCTCTCCGGGGA
CTGGAACCCGCTCCACGCCGACCCGGCCTTCGCCAAGCTCGCCGGCTTCGACCGGCCGATCCTGCACGGACTGTGCACGT
ACGGCATGGTCCTCAAGGCCGTCACCGACACCCTGCTGGACGGCGACGTCTCCCGGATCGCCGCCTACCGCACCCGCTTC
GCCGGAGTGGTCTTCCCCGGCGAGACCCTCCGCATCCGGATGTGGCAGGTCGGGGACGGGCGCGTCCAGGTGGCCGTGAC
CGCCGCCGGACGGGACGACGCCCCGGTCCTCGCGGACACGCTCGTCGAACACTCC

Fig.5

SEQ ID NO: 5
AGTAAGCTTCAAAGGAGGGAAAGTATGGCGTCAAAGGATAGCTTCG
SEQ ID NO: 6
ATTGGGCCCTTCGCTCATCAGTCTACTTCTCC
SEQ ID NO: 7
AGTAAGCTTCAAAGGAGGGAAAGTATGGCGTCAAAGGATAGCTT
SEQ ID NO: 8
TATGGGCCCATTTAAATCTACTTCTCCAAAACGTACG
SEQ ID NO: 9
ATCATTTAAATAGGAGGGAAAGTATGCCCATCGATGCCCGAGC
SEQ ID NO: 10
AGCATTTAAATTCAGGAGTGTTCGACGAGCGTGTC

Fig.8
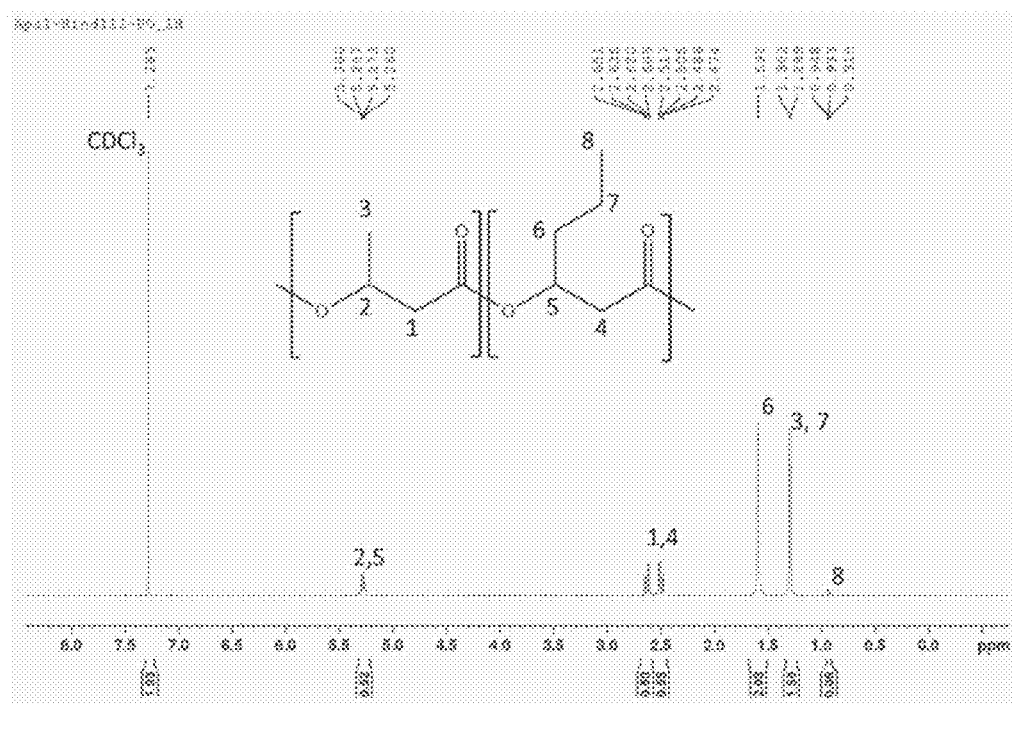
(a)
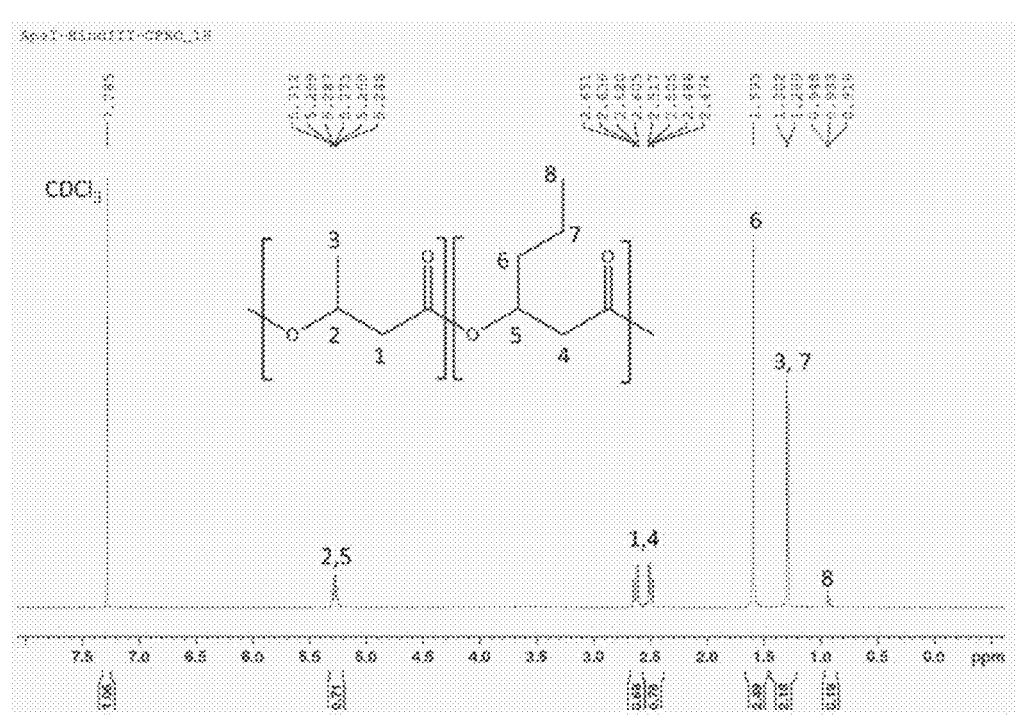
(b)

Fig. 9
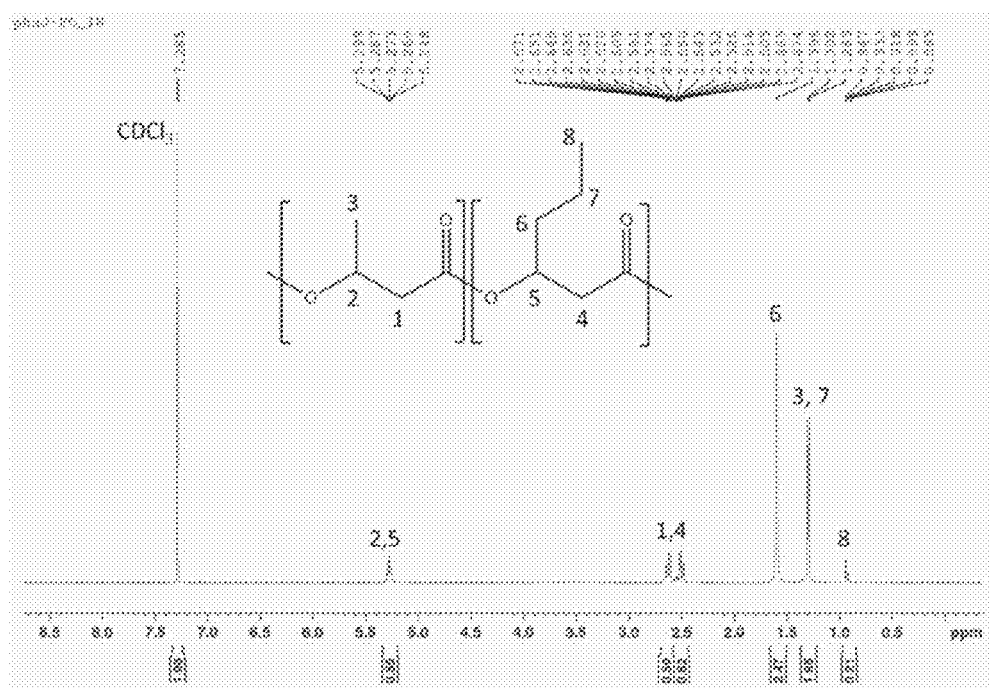
(a)
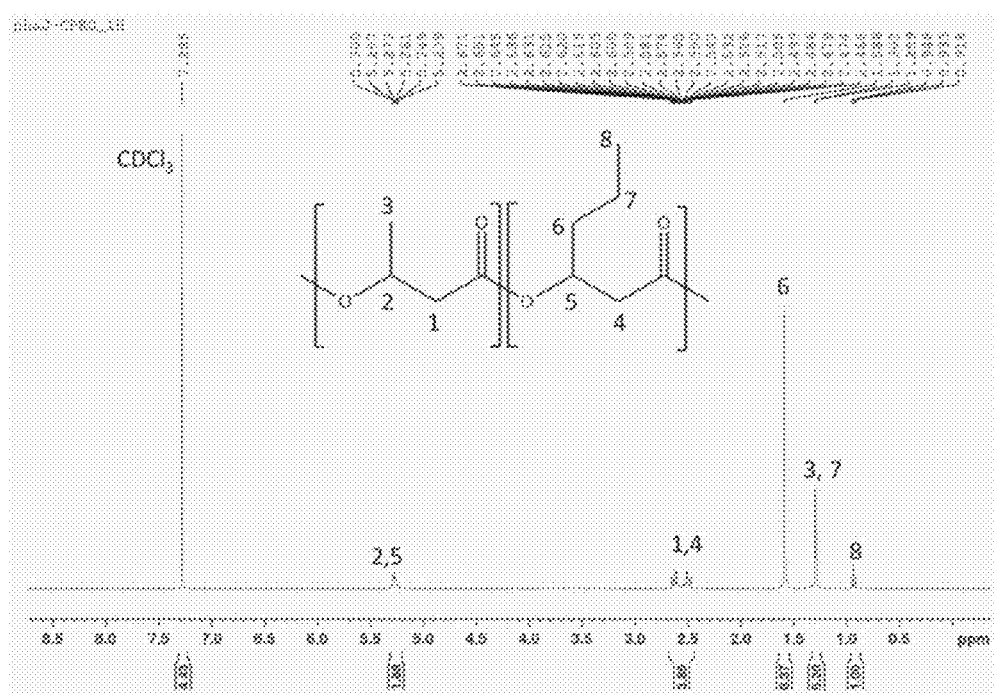
(b)

RECOMBINANT VECTOR COMPRISING GENE FOR SYNTHESIZING HIGH MOLECULAR WEIGHT COPOLYMER, TRANSFORMANT AND METHOD FOR PRODUCING POLYMERS USING TRANSFORMANT, RECOMBINANT STRAINS HAVING GENE FOR SYNTHESIZING HIGH MOLECULAR WEIGHT COPOLYMERS IN GENOME AND METHOD FOR PRODUCING POLYMERS USING RECOMBINANT STRAIN

The instant application contains a Sequence Listing which has been submitted electronically in ASCII format and is hereby incorporated by reference in its entirety. Said ASCII copy, created on May 6, 2022, is named YKN-0013FNC Amended_Sequence_Listing_as_filed.txt and is 12 k bytes in size.

TECHNICAL FIELD

The present invention relates to a gene that encoding polymer synthase from mangrove soil metagenome and a gene that encoding enoyl-CoA hydratase from *Streptomyces* sp. CFMR 7 (Accession number: CP011522). In more details, this invention details out these functional genes that encode for a polymer synthase and enoyl-CoA hydratase, respectively, the recombinant vectors, that harbours either the polymer synthase gene only or both genes, a transformant bacterial strain that expresses these vectors and the process of producing the polymer via these functional genes.

BACKGROUND ART

Polyhydroxyalkanoates (PHAs) are biopolyesters produced from microorganisms (bacteria and archaea) under nutrient limitations and stress conditions as storage compounds (carbon reserve). Besides possessing physicochemical properties similar to the petrochemical-derived plastics, the major advantages of PHA compared to the synthetic plastics are its biodegradability, biocompatibility and sustainability. The key enzyme that is involved in the polymerization of PHA is PHA synthase (PhaC). PhaC is an interesting enzyme because it can polymerize high molecular weight hydrophobic PHA chains in the hydrophilic environment of the cell cytoplasm.

In the current knowledge on the diversity of PHA, PHA producers and PhaC comes mostly from studies on pure microbial isolates using culture-dependent approaches. A total of four classes of PhaC and 167 PHA producers, based on genus have been reported from the existing cultivable soil microorganisms which are believed to be not more than 15% of the total soil microorganisms. The remaining 85% is still unexplored. Therefore, there is a huge knowledge gap in understanding the diversity PHA producers from this pool of unexplored microbial community.

The mangrove soil biome contains high microbial diversity and is continuously exposed to various abiotic stresses such as saline and anoxic conditions. Some studies have reported the isolation of PHA producers from the mangrove environment. However, no study on PhaC from mangrove soil metagenomes has been reported. Therefore, there is a strong chance to discover large numbers of novel PhaCs from new microbial genera in the mangrove soil metagenome, particularly from the anaerobic microorganisms.

The properties of PHA can be tailore to suit various applications by controlling the incorporation and/or composition of secondary monomers. Bacterial PHA can be divided into three main types depending on the number of carbon atoms in the monomeric units: short-chain-length (scl), medium-chain-length (mcl) and a combination of scl-mcl. The scl-PHAs consist of 3-5 carbon atoms, mcl-PHAs have 6-14 carbon atoms whereas the number of carbon atoms in scl-mcl-PHAs can range from 3-14 per monomer. The type of the PHA produced is depend on the substrate specificity of the polymer synthase. PHAs composed of mostly scl monomers are often stiff and brittle, whereas PHAs composed of mostly mcl monomers are elastomeric in nature. Scl-mcl PHA copolymers can have properties between the two states, dependent on the ratio of scl and mcl monomers in the copolymer.

The enoyl-CoA hydratase encoded by phaf exhibited the (R)-specific hydratase activity which turn out for supplying (R)-3-hydroxyacyl-CoA monomer units e.g. 3-hydroxyhexanoate coenzyme A (3HHx-CoA) from fatty acid β-oxidation to poly(3-hydroxybutyrate-co-3-hydroxyhexanoate) [P(3HB-co-3HHx)] during biosynthesis.

There are some patented technologies over the prior arts relating to a polymer synthase and the gene coding therefor. U.S. Pat. No. 6,812,013 B2 relates to a PHA synthase useful in a process for preparing a PHA, a gene encoding this enzyme, a recombinant vector comprising the gene, a transformant transformed by the vector, a process of producing a PHA synthase utilizing the transformant and a process for preparing a PHA utilizing the transformant. This invention is characterized by a transformant obtained by introducing a PHA synthase gene from *Pseudomonas putida* into a host microorganism which is cultured to produce a PHA synthase or PHA.

Another U.S. Patent No. US2004/0146998 A1 also relates to transformant and process for producing polymer by using the same. This invention discloses a gene encoding for a copolymer-synthesizing enzyme, a microorganism which utilizes the gene for the fermentative synthesis of a polymer and a method of producing a polymer with the aid of microorganism. This invention focuses on the construction of the transformant which comprises polyester synthesis-associated enzyme gene, a promoter and a terminator and has been introduced into yeast.

An improved transformant and process for producing polymer using the same are disclosed in EP Patent No. EP1626087 A1. This invention provides a gene expression cassette which comprises a gene coding for an Aeromonas caviae-derived PHA synthase. Yeast is also used as a host and a mutation has been introduced in the promoter and terminator do as to allow the gene cassette to be functioning in the yeast.

Some of the patented technologies disclose a combination between polymer synthase encoding gene and other genes. U.S. Patent No. US2008/0233620 A1 relates to a transformant and a process for producing a gene expression product in yeast. The transformant is obtained by introducing a plurality of enzyme genes involved in PHA synthesis such as a combination of PHA synthase and an acetoacetyl CoA reductase gene. In another U.S. Patent No. US2003/146703 a recombinant microorganism expressing both PHA synthase and intracellular PHA depolymerase is disclosed. This invention allows the simultaneous synthesis and degradation of PHA.

The U.S. Patent No. US2012/0088280 A1 describes a novel polymer synthase derived from *Chromobacterium* sp. and the gene responsible to encode the enzyme, a recombinant vector harbouring the gene, a transformant transformed with the vector and the process of producing plastic-like polymers by using this transformant.

Most of the patented technologies relate to a transformant and a process of producing polymer or PHA using the transformant disclosed. However, these patented technologies involved PHA synthase genes which are derived from a different region of the genome of a different species of organism. Thus far, there is also no patented technology disclosing the isolation of polymer synthase from metagenomic DNA. It is therefore desirable for the present invention to provide an improved DNA fragment of the polymer synthase gene to produce a recombinant vector and a transformant which can be useful in providing polymer synthase with broad substrate specificity for production of PHA with properties that can be tailored to suit various applications.

SUMMARY OF INVENTION

Technical Problem

The primary object of the present invention is to provide a polymer synthase gene which is derived from mangrove soil metagenome, and the method for producing the useful copolymer by using this polymer synthase.

Another object of the present invention is to provide an enoyl-CoA hydratase gene which is derived from *Streptomyces* sp. CFMR 7, and the method for producing the useful copolymer, P(3HB-co-3HHx) with increasing the composition of 3HHx by the expression of this enoyl-CoA hydratase.

Still another object of the present invention is to develop a more efficient method for producing 3HHx copolymers with higher molecular weight by using the transformant containing the polymer synthase.

Yet another object of the present invention is to develop a more efficient method for producing copolymers with lipase-degradable monomer sequences such as 4HB and 5HV by using the transformant containing the polymer synthase.

Solution to Problem

The present invention discloses an isolated polynucleotide encoding for polypeptide comprising an amino acid sequences set forth in SEQ ID NO: 1, or an amino acid sequences set forth in SEQ ID NO: 1 wherein one or more amino acids is replaced, deleted or added, the polypeptide having polymer synthase activity.

According to the preferred embodiment of the present invention, the isolated polynucleotide comprises a nucleotide sequence set forth in SEQ ID NO: 2, or a nucleotide sequence set forth in SEQ ID NO: 2 wherein one or more nucleotides is replaced, deleted or added; or the complementary sequence thereof.

Still another preferred embodiment of the present invention is an isolated polynucleotide comprising a nucleotide sequence set forth in SEQ ID NO: 2, or a nucleotide sequence set forth in SEQ ID NO: 2 wherein one or more nucleotides is replaced, deleted or added; wherein T is replaced by U; or the complementary sequence thereof.

Another present invention discloses an isolated polynucleotide encoding for polypeptide comprising an amino acid sequences set forth in SEQ ID NO: 3, or an amino acid sequences set forth in SEQ ID NO: 1 wherein one or more amino acids is replaced, deleted or added, the polypeptide having polymer synthase activity.

According to the preferred embodiment of the present invention, the isolated polynucleotide comprises a nucleotide sequence set forth in SEQ ID NO: 4, or a nucleotide sequence set forth in SEQ ID NO: 2 wherein one or more nucleotides is replaced, deleted or added; or the complementary sequence thereof.

Still another preferred embodiment of the present invention is an isolated polynucleotide comprising a nucleotide sequence set forth in SEQ ID NO: 4, or a nucleotide sequence set forth in SEQ ID NO: 4 wherein one or more nucleotides is replaced, deleted or added; wherein T is replaced by U; or the complementary sequence thereof.

Yet another embodiment of the present invention is a recombinant vector comprising the isolated polynucleotide as set forth in the preceding embodiments. Preferably, the recombinant vector is a plasmid or phage.

In a further embodiment of the present invention, a transformant by the vector as set forth in the preceding embodiments is disclosed.

Yet another embodiment of the present invention is a recombinant strain with genome comprising the isolated polynucleotide as set forth in the preceding embodiments.

Another further embodiment of the present invention is a process for producing polymer comprising: culturing the transformant or the recombinant strain as set forth in the preceding embodiments in a medium containing polymerizable materials; and recovering the polymer from the cultured medium. Preferably, the polymer is PHA.

BRIEF DESCRIPTION OF DRAWINGS

FIG. 1 is the amino acid sequence of the polypeptide of polymer synthase as described in one of the preferred embodiments of the present invention;

FIG. 2 is the nucleotide sequence of the polynucleotide encoding the polymer synthase as described in one of the preferred embodiments of the present invention;

FIG. 3 is the amino acid sequence of the polypeptide of enoyl-CoA hydratase as described in one of the preferred embodiments of the present invention;

FIG. 4 is the nucleotide sequence of the polynucleotide encoding the enoyl-CoA hydratase as described in one of the preferred embodiments of the present invention;

FIG. 5 is the nucleotide sequences of the amplification nucleotides used for the PCR amplification of the polymer synthase as described in one of the preferred embodiments of the present invention;

FIG. 6 (b) is the $^1$H NMR spectrum P(3-hydroxybutyrate-co-3-hydroxyhexanoate), one of the copolymers synthesized by the transformant as described in one of the embodiments of the present invention;

FIG. 8 is $^1$H NMR analysis of polymers produced using transformant without phaJ (PUB$^-$4/pBBR1MCS2_$C_{BP\text{-}M\text{-}CPF4}$) and (a) PO and (b) CPKO as carbon sources; and FIG. 9 is $^1$H NMR analysis of polymers produced using transformant with phaJ (PHB$^-$4/pBBRMCS2_$C_{BP\text{-}M\text{-}CPF4}$_$J_{Ss}$) and (a) PO and (b) CPKO as carbon sources.

DESCRIPTION OF EMBODIMENTS

Figure 6:
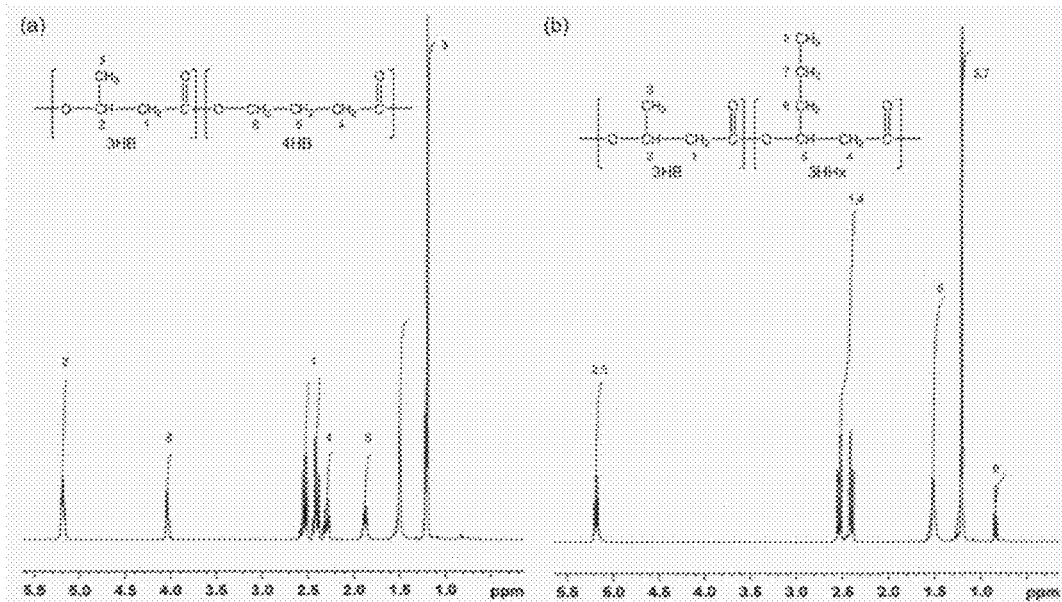
FIG. 6 (a) is the $^1$H NMR spectrum P(3-hydroxybutyrate-co-4-hydroxybutyrate), one of the copolymers synthesized by the transformant as described in one of the embodiments of the present invention.

One skilled in the art will readily appreciate that the present invention is well adapted to carry out the objects and obtain the ends and advantages mentioned, as well as those inherent therein. The embodiments described herein are not intended as limitations on the scope of the invention.

For the purpose of facilitating an understanding of the invention, there is illustrated in the accompanying drawing the preferred embodiments from an inspection of which when considered in connection with the following description, the invention, its construction and operation and many of its advantages would be readily understood and appreciated.

The present invention relates to a gene that encoding polymer synthase from mangrove soil metagenome and a gene that encoding enoyl-CoA hydratase from *Streptomyces* sp. CFMR 7. In more details, this invention details out these functional genes that encode for a polymer synthase and enoyl-CoA hydratase, respectively, the recombinant vectors, that harbours either the polymer synthase gene only or both genes, a transformant bacterial strain that expresses these vectors and the process of producing the polymer via these functional genes.

The present invention describes a novel PhaC [Pha $C_{BP-M-CPF4}$ (Accession number: AXB72506)] with extremely wide substrate specificity that was discovered from the Balik Pulau (Penang, Malaysia) mangrove soil. It could produce scl-PHA copolymers, poly(3-hydroxybutyrate-co-3-hydroxyvalerate) random copolymer [P(3HB-co-3HV)], poly(3-hydroxybutyrate-co-3-hydroxy-4-methylvalerate) random copolymer [P(3HB-co-3H4MV)], poly(3-hydroxybutyrate-co-4-hydroxybutyrate) random copolymer [P(3HB-co-4HB)] and poly(3-hydroxybutyrate-co-5-hydroxyvalerate) random copolymer [P(3HB-co-5HV)]. This PHA synthase is suitable for the biosynthesis of PHAs that can be used in various biomedical applications due to its ability to incorporate the lipase-degradable monomer sequences of 4HB and 5HV. Besides, this PHA synthase also produced P(3HB-co-3HHx), the copolymer has been identified as a commercially useful PHA copolymer that has similar properties to commodity plastics such as polypropylene (PP) and low-density polyethylene (LDPE).

The present invention also describes a PhaJ [PhaJ$_{Ss}$, (Accession number: ALC30197)] that can supply the mcl monomers for polymerization of PHA. This PhaJ was discovered from *Streptomyces* sp. strain CFMR 7. It exhibited the (R)-specific hydratase activity which turn out for supplying 3HHx-CoA from fatty acid β-oxidation to P(3HB-co-3HHx) during biosynthesis.

Hereinafter, the invention shall be described according to the preferred embodiment of the present invention and by referring to the accompanying description and drawings. However, it is to be understood that limiting the description to the preferred embodiments of the invention and to the drawings is merely to facilitate discussion of the present invention and it is envisioned that those skilled in the art may devise various modifications without departing from the scope of the appended claim.

The present invention discloses an isolated polynucleotide encoding for a polypeptide comprising an amino acid sequence set forth in SEQ ID NO: 1 with polymer synthase activity. SEQ ID NO: 1 is illustrated in FIG. 1.

According to the preferred embodiment of the present invention, the isolated polynucleotide is a polymer synthase gene. Besides, this polymer synthase gene can encode a polypeptide containing the amino acid sequence of SEQ ID NO: 1, or a sequence where one or more amino acids are deleted from, replaced with or added to the amino acid sequence of SEQ ID NO: 1. Even if one or more amino acids in the sequence of SEQ ID NO: 1 may have undergone mutations such as deletion, replacement, or addition, the polynucleotide encoding for a polypeptide containing the amino acid sequence is contained in the gene of the present invention insofar as the polypeptide has polymer synthase activity. For example, polynucleotide encoding for the amino acid sequence of SEQ ID NO: 1 where methionine at the first position is deleted is also contained in the gene of the present invention. In other words, the gene of the present invention encompasses not only the nucleotide sequence encoding for the amino acid sequence of SEQ ID NO: 2 but also its degenerated which except for degeneracy codons, code for the same polypeptide. The abovementioned mutations such as deletion, replacement or addition can be induced by known site-directed mutagenesis.

In a preferred embodiment of the present invention, an isolated polynucleotide comprising a nucleotide sequence set forth in SEQ ID NO: 2 or the complementary sequence thereof is disclosed. SEQ ID NO: 2 is shown in FIG. 2. Still another embodiment of the present invention is an isolated polynucleotide which comprises a nucleotide sequence set forth in SEQ ID NO: 2, wherein T is replaced by U; or the complementary sequence thereof. These polynucleotides are coding for a polypeptide with polymer synthase activity.

This polymer synthase gene is preferably cloned from a mangrove soil metagenome. In accordance with the preferred embodiment of the present invention, the polymer synthase gene is isolated from a total soil DNA obtained from mangrove soil. The gene of the present invention can be obtained by polymerase chain reaction (PCR) amplification technique using mangrove soil metagenomic DNA as template, or by hybridization using a DNA fragment having the nucleotide sequence as a probe.

In accordance with the preferred embodiment of the present invention, PCR is used as the preferred method to obtain the DNA fragment of the polymer synthase gene using total mangrove soil metagenomic DNA as template. Initially, the metagenomic DNA is extracted from a fresh mangrove soil samples. It is known in the art that isolation of metagenomic DNA involves the use of commercially available kits such as the MoBio PowerSoil DNA isolation kit and the determination of the total metagenomic DNA sequence using shotgun metagenomic sequencing. To obtain a DNA fragment that comprises of the polymer synthase gene from the soil metagenome, a probe is preferably prepared. Well conserved regions of the polymer synthase gene are selected from known amino acid sequences and the nucleotide sequences coding for them can be used to design oligonucleotides. A primer pair of amplification nucleotide is designed to achieve this purpose. The sequence of the primer pair is shown in FIG. 5 in which SEQ ID No: 5 is used as forward primer and SEQ ID No: 6 is used as reverse primer.

For cloning the polymer synthase gene into the vector, a restriction site, SwaI, was added to the behind of the polymer synthase gene in the vector by design the primer with SwaI restriction site at the behind stop codon of the polymer synthase gene sequence and in front of the ApaI restriction site. A primer pair of amplification nucleotide is designed to achieve this purpose. The sequence of the primer pair is shown in FIG. 5 in which SEQ ID No: 7 is used as forward primer and SEQ ID No: 8 is used as reverse primer.

The amplified DNA fragment can be digested with appropriate restriction enzymes such as HandeI and ApaI. The DNA fragment is then ligated into a suitable vector which has been previously cleaved with the restriction enzymes, which can be HindIII and ApaI. The vector is dephosphorylated by treatment with alkaline phosphatase before the ligation.

Yet another embodiment of the present invention is a recombinant vector comprising an isolated polynucleotide, wherein the isolated polynucleotide is encoding for a polypeptide comprising an amino acid sequence set forth in SEQ ID NO: 1 with polymer synthase activity; or a polypeptide comprising an amino acid sequence set forth in SEQ ID NO: 1, wherein one or more amino acids is replaced, deleted, replaced or added, the polypeptide having polymer synthase activity.

In accordance with the preferred embodiment of the present invention, plasmid capable of autonomously replicating in host microorganism is used as vector. The plasmid that can be applied as vector includes pBBR1MCS2 and pBBR1-I-GG18 (pBBR1MCS2-derivative cloning vector). These vectors are obtained from modifications of commercially available vectors. Vectors capable of autonomously replicating in 2 or more host cells such as *Escherichia coli* or *Bacillus brevis*, as well as various shuttle vectors, can also be used. Such vectors are also cleaved with the restriction enzymes so that their fragment can be obtained.

Accordingly, conventional DNA ligase kit is used to ligate the DNA fragment with the vector fragment. The DNA fragment is annealed and ligated with the vector fragment to produce recombinant vector.

Another present invention discloses an isolated polynucleotide encoding for a polypeptide comprising an amino acid sequence set forth in SEQ ID NO: 3 (R)-specific hydratase activity. SEQ ID NO: 3 is illustrated in FIG. 3.

According to the preferred embodiment of the second invention, the isolated polynucleotide is enoyl-CoA hydratase gene. Besides, this enoyl-CoA hydratase gene can encode a polypeptide containing the amino acid sequence of SEQ ID NO: 3, or a sequence where one or more amino acids are deleted from, replaced with or added to the amino acid sequence of SEQ ID NO: 3. Even if one or more amino acids in the sequence of SEQ ID NO: 3 may have undergone mutations such as deletion, replacement, or addition, the polynucleotide encoding for a polypeptide containing the amino acid sequence is contained in the gene of the present invention insofar as the polypeptide has (R)-specific hydratase activity. For example, polynucleotide encoding for the amino acid sequence of SEQ ID NO: 3 where methionine at the first position is deleted is also contained in the gene of the present invention. In other words, the gene of the present invention encompasses not only the nucleotide sequence encoding for the amino acid sequence of SEQ ID NO: 4 but also its degenerated which except for degeneracy codons, code for the same polypeptide. The abovementioned mutations such as deletion, replacement or addition can be induced by known site-directed mutagenesis.

In a preferred embodiment of the present invention, an isolated polynucleotide comprising a nucleotide sequence set forth in SEQ ID NO: 4 or the complementary sequence thereof is disclosed. SEQ ID NO: 4 is shown in FIG. 4. Still another embodiment of the present invention is an isolated polynucleotide which comprises a nucleotide sequence set forth in SEQ ID NO: 4, wherein T is replaced by U; or the complementary sequence thereof. These polynucleotides are coding for a polypeptide with (R)-specific hydratase activity.

This enoyl-CoA hydratase gene is preferably cloned from *Streptomyces* sp. CFMR 7. The gene of the present invention can be obtained by polymerase chain reaction (PCR) amplification technique using *Streptomyces* sp. CFMR 7 genomic DNA as template. A primer pairs of amplification nucleotide is designed to achieve this purpose. The sequence of the primer pair is shown in FIG. 5 in which SEQ ID No: 9 is used as forward primer and SEQ ID No: 10 is used as reverse primer.

The amplified DNA fragment can be digested with appropriate restriction enzymes such as SwaI. The DNA fragment is then ligated into a suitable vector which has been previously cleaved with the restriction enzymes, which can be SwaI. The vector is dephosphorylated by treatment with alkaline phosphatase before the ligation.

Yet another embodiment of the present invention is a recombinant vector comprising an isolated polynucleotide, wherein the isolated polynucleotide is encoding for a polypeptide comprising an amino acid sequence set forth in SEQ ID NO: 3 with (R)-specific hydratase activity; or a polypeptide comprising an amino acid sequence set forth in SEQ ID NO: 3, wherein one or more amino acids is replaced, deleted, replaced or added, the polypeptide having (R)-specific hydratase activity.

In accordance with the preferred embodiment of the present invention, plasmid capable of autonomously replicating in host microorganism is used as vector. The plasmid that can be applied as vector includes pBBR1MCS2 and pBBR1-I-GG18 (pBBR1MCS2-derivative cloning vector). These vectors are obtained from modifications of commercially available vectors. Vectors capable of autonomously replicating in 2 or more host cells such as *Escherichia coli* or *Bacillus brevis*, as well as various shuttle vectors, can also be used. Such vectors are also cleaved with the restriction enzymes so that their fragment can be obtained.

Accordingly, conventional DNA ligase kit is used to ligate the DNA fragment with the vector fragment. The DNA fragment is annealed and ligated with the vector fragment to produce recombinant vector.

In a further embodiment of the present invention, a transformant is obtained by introducing the recombinant vector into suitable host strains that are compatible with the expression vector that is constructed using the said recombinant vector. The present invention is not limited to the use of a particular host strain as long as it can express the target gene in the recombinant vector. Some examples of microorganism that are suitable for this are those belonging to the genus *Cupriavidus, Bacillus, Pseudomonas* (bacteria), *Saccharomyces* and *Candida* (yeast), COS and CHO cell lines (animal cells).

If bacteria belonging to the genus *Cupriavidus* or *Pseudomonas* are used as host strain, it is preferred that the recombinant DNA of the present invention to have been constituted in such a way that it consists of a suitable promoter, the DNA fragment of the present invention, and a transcription termination sequence to ensure autonomous replication in the host. Preferably, the expression vectors consist of but not limited to pGEM-T and pBBR1MCS-2 derivatives. Likewise, the promoter can be of any type provided that it can be expressed in the host. Examples of promoters which are derived from *Cupriavidus necator, E. coli* or phage include putative *C. necator* promoter, trp promoter, lac promoter, PL promoter, pR promoter and T7 promoter.

Any established methods can be used to introduce recombinant vector into the host microorganism. For instance, if the host microorganism is *E. coli*, the calcium method and the electroporation methods can be used. If phage DNA is used, the in vitro packaging method can be adopted.

Expression vectors such as Yep13 or YCp50 are employed if yeast is used as the host. Accordingly, the promoter can be gal 1 promoter or gal 10 promoter; and the method for introducing the recombinant DNA into yeast includes the electroporation method, the spheroplast method and the lithium acetate method. If animal cells are used as the host, expression vectors such as pcDNAI or pcDNAI/Amp are used. Accordingly, the method for introducing the recombinant DNA into animal cells can be the electroporation method or the potassium phosphate method.

The present invention also discloses a process for producing polymers involving the steps of culturing a transformant harbouring a DNA as set forth in any of the preceding embodiments in a medium comprising of polymerizable compounds; and recovering the polymer that is formed and accumulated in the transformant.

A conventional method used to culture the host is also used to culture the transformant. The medium for the transformant is also used for the microorganisms belonging to the genus *Cupriavidus* and *Pseudomonas* as the host include a medium containing a carbon source assimilable by the microorganism, in which a nitrogen source, inorganic salts or another organic nutrition sources has been limited, for example a medium in which the nutrition source is in a range of 0.01% to 0.1% by weight of the medium.

The carbon source is necessary for growth of the microorganism, and it is simultaneously a starting material of carbons such as glucose, fructose, sucrose or maltose. Further, fat- and oil-related substances having two or more carbon atoms can also be used as the carbon source. The fat- and oil-related substances include natural fats and oils, such as corn oil, soybean oil, safflower oil, sunflower oil, olive oil, coconut oil, palm oil, rape oil, fish oil, whale oil, porcine oil and cattle oil; aliphatic acids such as acetic acid, propionic acid, butanoic acid, pentanoic acid, hexoic acid, octanoic acid, decanoic acid, lauric acid, oleic acid, palmitic acid, linolenic acid, linolic acid and myristic acid; alcohols such as ethanol, propanol, butanol, pentanol, hexanol, octanol, lauryl alcohol, oleyl alcohol and palmityl alcohol as well as esters thereof. Meanwhile, the salts, peptone, meat extract, yeast extract or corn steep liquor. The inorganic matter includes sodium dihydrogen phosphate, disodium hydrogen phosphate, potassium dihydrogen phosphate, potassium sulphate, monopotassium phosphate, dipotassium phosphate, magnesium phosphate, calcium chloride, magnesium sulphate and ammonium chloride.

The culture is preferably carried out under aerobic conditions with shaking at 30° C. to 34° C. for more than 24 hours, preferably 1 to 3 days, after expression is induced. During culture, antibiotics such as ampicillin, kanamycin, gentamycin, antipyrine or tetracycline can be added to the culture. Accordingly, the polymer can be accumulated in the microorganism, and the polymer can then be recovered.

To culture the microorganism transformed with the expression vector using an inducible promoter, its inducer, such as isopropyl-β-D-thiogalactopyranoside (IPTG) or indoleacrylic acid (IAA), can also be added to the medium. To culture transformant from animal cells as the host, medium such as RPMI-1640 or DMEM supplemented with fetal bovine serum can be used. According to the preferred embodiment of the present invention, culture is carried out usually in the presence of 5% $CO_2$ at 30° C. to 37° C. for 14 to 28 days. During culture, antibiotics such as kanamycin or penicillin may be added to the medium.

In accordance with the preferred embodiment of the present invention, a polymer purification step can also be carried out. Preferably, the transformant is recovered from the culture by centrifugation, the washed with distilled water and hexane, and dried. Thereafter, the dried transformant is suspended in chloroform and heated to extract the polymer therefrom. The residues can are removed by filtration. Preferably, methanol is added to this chloroform solution to precipitate polymer. After the supernatant is removed by filtration or centrifugation, the precipitates are dried to give purified polymer. The resulting polymer is confirmed to be the desired one in a usual manner, for instance, by gas chromatography, nuclear magnetic resonance or others.

This polymer synthase can synthesize a copolymer (polymer) consisting of a monomer unit 3-hydroxyalkonoic acid represented by Formula I, wherein R represents a hydrogen atom or C1 to C4 alkyl group.

Chem. 1

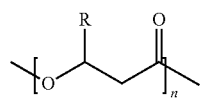

Formula I

Preferably, the polymer is polyhydroxyalkanoate. The polymer can be a copolymer including P(3HB-co-3HV random copolymer, [P(3HB-co-3HHx)] random copolymer, [P(3HB-co-3H4MV)] random copolymer, [P(3HB-co-4HB)] random copolymer and [P(3HB-co-5HV)] random copolymer.

The convention process for producing poly(3-hydroxybutyrate) [P(3HB)] causes problem in physical properties of inferior resistance to impact because this polymer is a highly crystalline polymer. Degree of crystallinity is lowered by introducing 3-hydroxyvalerate having 5 carbon atoms or 3-hydroxyhexanoate having 6 carbon atoms into a polymer chain. The polymer acts as a flexible polymeric material which is also excellent in thermostability and formability.

In the present invention, the P(3HB-co-3HHx) copolymer can be produced in high yield by use of the polymer synthase of BPM-CPF-4. Since the desired polymer can be obtained in a large amount using the above means, it can be used as a biodegradable material of yarn, film or various. Further, the gene of the present invention can be used to breed a strain highly producing the P(3HB-co-3HHx) copolymer.

In the present invention, the P(3HB-co-3HHx) copolymer can be produced in higher composition of 3HHx by co-express the enoyl-CoA hydratase with polymer synthase, in this case, polymer synthase of BPM-CPF-4. Since the desired polymer can be obtained in a large amount using the above means, it can be used as a biodegradable material of yarn, film or various. Further, the gene of the present invention can be used to breed a strain producing P(3HB-co-3HHx) copolymer with higher 3HHx composition.

In the present invention, the P(3HB-co-4HB) and P(3HB-co-5HV) copolymers can be produced in high yield by use of the polymer synthase of BPM-CPF-4. These copolymers be used in various biomedical applications due to its ability to incorporate the lipase-degradable monomer sequences of 4HB and 5HV.

The person disclosure includes as contained in the appended claims, as well as that of the foregoing description. Although this has been described in its preferred from with a degree of particularity, it is understood that the present disclosure of the preferred form has been made only by way of example and that numerous changes in the details of construction and the combination and arrangements of parts may be resorted to without departing from the scope of the invention.

EXAMPLE

Examples are provided below to illustrate different aspects and embodiments of the present invention. These examples are not intended in any way to limit the disclosed invention, which is limited only by the claims.

Example 1

Cloning of Polymer Synthase Gene from Mangrove Soil Metagenome

Initially, metagenomic DNA was isolated from mangrove soil directly using the MoBio PowerSoil DNA isolation kit.

Shotgun metagenomic sequencing was performed using 125 bp paired-end sequencing with the Illumina HiSeq 2000 platform. The raw sequences (unfiltered) were submitted to the metagenomics RAST server (MG-RAST) for automated sequence pre-processing (quality checking) and gene annotation. The metagenomic data was deposited in the MG-RAST database under the ID: mgm4512801.3 (BalikPulau_mangrove). For in silico gene mining of PHA synthases, all the sequences or reads (~120 to 260 bp) annotated as "PHA synthase" against the NCBI Reference Sequence (RefSeq) database were retrieved from the MGRAST server version 3 using five consensus keywords: hydroxybutyrate, hydroxyalkanoate, hydroxyalkanoic, PHA and PHB. All the annotation and sequence information were retrieved from the MG-RAST database via the MG-RAST RESTful API (Application Programming Interface). Complete or nearly full-length PHA synthase genes from the mangrove soil metagenomic data were obtained by conducting de novo DNA sequence assembly using SPAdes 3.5.0-Darwin (St. Petersburg genome assembler) on the subset of sequences that were previously annotated as PHA synthase. Assembled contigs with sizes more than 1 kb were selected for subsequent analyses. BLASTX was carried out against the GenBank non-redundant protein sequences database to search for similar sequences and determine the correct reading frames for the partial or complete PHA synthases.

To obtain a DNA fragment containing the polymer synthase gene from metagenomic DNA, a probe was then prepared. Two domain-specific oligonucleotides designed using NCBI database as a reference, SEQ ID NO:5 and SEQ ID NO:6, were synthesized.

The polymer synthase gene was amplified by PCR using these oligonucleotides as primers and the metagenomic DNA from mangrove soil as a template. The PCR conditions were as follow: 94° C. for 3 min; 30 cycles of 94° C. for 30 s, 57° C. for 30 s, and 72° C. for 2 min; and a final step at 72° C. for 10 min.

The nucleotide sequence of a 1.7 kbp HindIII-ApaI from this fragment was determined by the Sanger method. The polymer synthase gene containing the nucleotide sequence (1656) SEQ ID NO:1 was obtained.

Example 2

Preparation of C. necator Transformant

The HindIII-ApaI polymer synthase gene fragment was first inserted into a cloning vector pCR4-TOPO (Registered Trademark, Invitrogen, USA) previously cleaved with the same restriction enzyme. The fragment was then digested again with HindIII and ApaI restriction enzymes and the resulting HindIII-ApaI polymer synthase gene fragment was inserted into a recombinant vector pBBR1MCS-2 capable of expression in microorganisms belonging to the genus Cupriavidus, and the resulting recombinant plasmid was transformed into Cuprividus necator PHB⁻4 (DSM 541) (strain deficient in the ability to synthesize polymer) by the conjugation transfer method.

Firstly, the recombinant plasmid was used to transform E. coli S17-1 by the calcium chloride method. The recombinant E. coli thus obtained and C. necator PHB⁻4 were transconjugated. The recombinant E. coli and C. necator PHB⁻4 were culture overnight in 1.5 mL LB medium and nutrient rich medium at 30° C. and the respective culture, each 0.1 mL, were combine and cultured on a shaker at room temperature for 1 hour. The mixture was then incubated without shaking for 30 minutes, and subsequently shaken again for 30 minutes. This microbial mixture was plated on Simmon's citrate agar containing 300 mg/L kanamycin and cultured at 30° C. for 2 days.

Since C. necator PHB⁻4 is rendered resistant to kanamycin by transferring the plasmid in the recombinant E. coli into it, the colonies grown on the Simmon's citrate agar are a transformant of C. necator.

Example 3

Synthesis of Polymer by C. necator Transformants

C. necator transformant was inoculated into 50 mL mineral medium (0.25 g/L magnesium sulphate heptahydrate, 3.32 g/L disodium hydrogen phosphate, 2.8 g/L potassium dihydrogen phosphate, 0.5 g/L ammonium chloride) containing 1 ml/L of trace elements and incubated in a flask at 30° C. 50 mg/L kanamycin was added in the mediums for C. necator transformants and the microorganism were cultured for 48 hours.

Each of strains of C. necator transformant and PHB⁻4 was inoculated into the above mineral medium to which 10 g/L fructose and 6 g/L of crude palm kernel oil (CPKO) had been added, and each strain was cultured at 30° C. for 48 hours in a 250 mL flask. Precursor carbon sources was added for copolymer generation. 50 mg/L kanamycin was added in the mediums for C. necator transformants.

The cultures were recovered by centrifugation, washed with distilled water and hexane (in the presence of CPKO) and lyophilized, and the weight of the dried microorganisms was determined. 2 mL sulfuric acid/methanol mixture (15:85) and 2 mL chloroform were added to 15-20 mg of the dried microorganism, and the simple was sealed and heated at 100° C. for 140 minutes whereby the polymer in the microorganisms was decomposed into methylester. 1 mL distilled water was added thereto and vortexed vigorously. It was left and separated into 2 layers, and the lower organic layer was removed and analysed for its components by capillary gas chromatography through a capillary column. The PHA content was determined by gas chromatography (GC) using the Shimadzu GC-2010 system equipped with an SPB-1 column (Supelco, USA). The column temperature was initiated at 70° C. and then increased to 280° C. in continuous steps of 10° C./min. The PHA content and composition were quantified with caprylic acid methyl ester (CME) as an internal standard. The results are shown in Table 1.

Table 1 shows the biosynthesis of PHA by C. necator transformant from fructose, mixture of fructose with different added precursor carbon sources and CPKO.

TABLE 1

| Carbon source | Dry cell weight (g/L) | PHA content (wt %)[a] | Monomer composition (mol %) | | | | | |
|---|---|---|---|---|---|---|---|---|
| | | | 3HB | 3HV | 5HV | 4HB | 3H4MV | 3HHx |
| Fructose (10 g/L) | 3.7 ± 0.1 | 75 ± 9 | 100 | ND | ND | ND | ND | ND |
| Crude palm kernel oil (5 g/L) | 2.8 ± 0.2 | 62 ± 5 | 93 ± 0 | ND | ND | ND | ND | 7 ± 0 |
| Fructose (10 g/L) + sodium valerate (2 g/L) | 2.5 ± 0.1 | 58 ± 7 | 87 ± 1 | 13 ± 1 | ND | ND | ND | ND |
| Fructose (10 g/L) + sodium 5-hydroxyvalerate (2 g/L) | 3.8 ± 0.9 | 67 ± 8 | 77 ± 0 | ND | 23 ± 0 | ND | ND | ND |
| Fructose (10 g/L) + sodium 4-hydroxybutyrate (2 g/L) | 2.8 ± 0.1 | 58 ± 1 | 86 ± 1 | ND | ND | 14 ± 1 | ND | ND |
| Fructose (10 g/L) + gamma-butyrolactone (2 g/L) | 3.7 ± 0.1 | 66 ± 2 | 100 | ND | ND | ND | ND | ND |
| Fructose (10 g/L) + isocaproic acid (1 g/L) | 1.6 ± 0.0 | 45 ± 5 | 90 ± 1 | ND | ND | ND | 10 ± 1 | ND |
| Fructose (10 g/L) + sodium hexanoate (2 g/L) | 1.9 ± 0.1 | 44 ± 1 | 82 ± 2 | ND | ND | ND | ND | 18 ± 2 |

3% inoculum from starter cultures (O.D = ~4.5) was transferred into 50 mL MM in 250 mL conical flask and incubated at 30° C., 48 hours, 200 rpm. The values reported are averages from triplicate cultures ± SDs.
[a]PHA content in freeze-dried cells
3HB, 3-hydroxybutyrate;
3HV, 3-hydroxyvalerate;
5HV, 5-hydroxyvalerate;
4HB, 4-hydroxybutyrate;
3H4MV, 3-hydroxy-4methylvalerate;
3HHx, 3-hydroxyhexanoate Based on the result in Table 1, the transformant could utilize fructose for the production of P(3HB) homopolymer. Cell dry weight of 3.7±0.1 g/L and polymer content of 75±9% by weight of the microorganism. Lower cell dry weight was obtained when CPKO was used as the sole carbon source. The cell biomass of the transformant was 2.8±0.2 g/L and the polymer content was 62±5% by weight of the microorganism. Interestingly, in the presence of CPKO, accumulation of P(3HB-co-3HHx) copolymer with 7 mol % of 3HHx was observed in the transformant.

To investigate the production of P(3HB-co-3HV) copolymer, sodium valerate was added to the culture supplemented with fructose. The 3HV composition generated by the transformant was 13±1 mol %. The cell biomass of the transformant was 2.5±0.1 g/L and the polymer content produced by this transformant was 58±7% by weight of the microorganism.

To investigate the production of P(3HB-co-5HV) copolymer, sodium 5-hydroxyvalerate was added to the culture supplemented with fructose. The 5HV composition generated by the transformant was 23±0 mol %. The cell biomass of the transformant was 3.8±0.9 g/L and the polymer content produced by this transformant was 67±8% by weight of the microorganism.

To investigate the production of P(3HB-co-4HB) copolymer, sodium 4-hydroxybutyrate was added to the culture supplemented with fructose. The 4HB composition generated by the transformant was 14±1 mol %. The cell biomass of the transformant was 2.8±0.1 g/L and the polymer content produced by this transformant was 58±1% by weight of the microorganism.

Also, to investigate the production of P(3HB-co-4HB) copolymer, gamma-butyrolactone was added to the culture supplemented with fructose. Only homopolymer P(3HB) was generated by the transformant. The cell biomass of the transformant was 3.7±0.1 g/L and the polymer content produced by this transformant was 66±2% by weight of the microorganism To investigate the production of P(3HB-co-3H4MV) copolymer, isocaproic acid was added to the culture supplemented with fructose. The 3HV composition generated by the transformant was 10±1 mol %. The cell biomass of the transformant was 1.6±0.0 g/L and the polymer content produced by this transformant was 45±5% by weight of the microorganism.

To investigate the production of P(3HB-co-3HHx) copolymer, sodium hexanoate was added to the culture supplemented with fructose. The 3HHx composition generated by the transformant was 18±2 mol %. The cell biomass of the transformant was 1.9±0.1 g/L and the polymer content produced by this transformant was 44±1% by weight of the microorganism.

Approximately one gram of lyophilized cell was mixed with 50 mL of chloroform and stirred at room temperature for three days. The mixture was filtered using Whatman No. 1 filter papers to remove cell debris. The resulting clear solution was then added dropwise into vigorously stirring ice-cold methanol to precipitate the PHA polymers. The precipitated polymers were separated from the methanol solution using vacuum filtration and then dried overnight at room temperature. Solvent extraction of PHA from the bacterial cells was usually able to produce the highest purity (95 to 100%) of PHA polymers.

Figure 7:
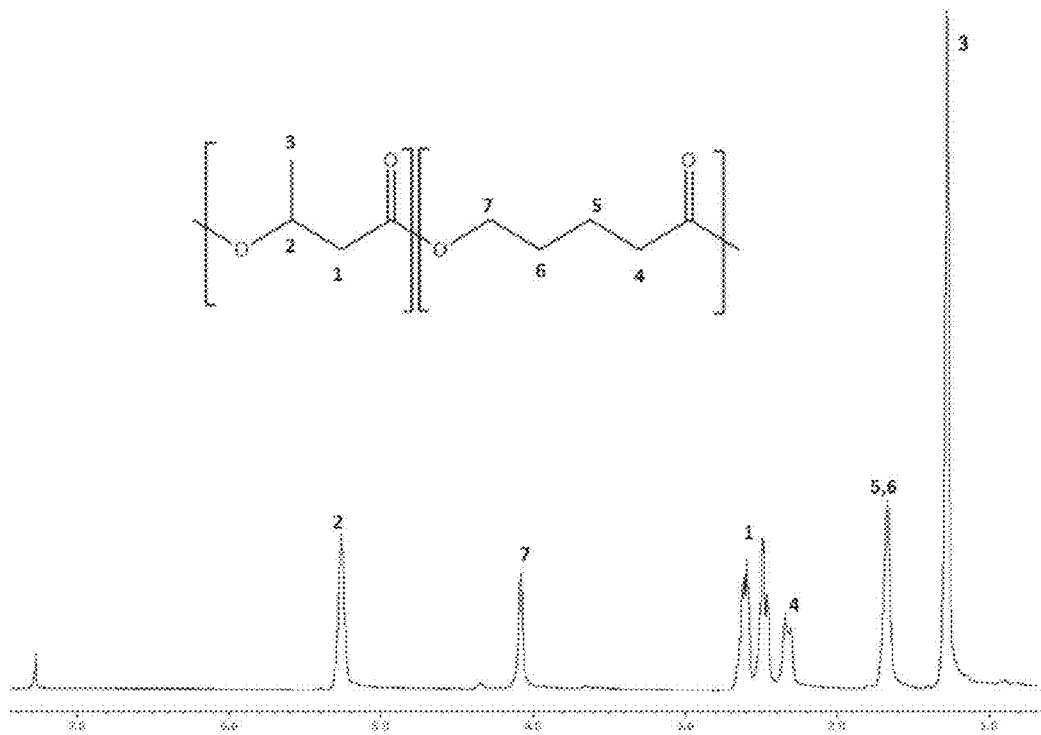
FIG. 7 is the $^1$H NMR spectrum P(3-hydroxybutyrate-co-5-hydroxvalerate), one of the copolymers synthesized by the transformant as described in one of the embodiments of the present invention.

The resulting polymer is confirmed by nuclear magnetic resonance. A total of 25 mg of polymer sample is dissolved in 1 mL of deuterated chloroform ($CDCL_3$). PHA polymers were analyzed by $^1$NMR spectroscopy using a Bruker AVANCE 500 (USA) operating at 500 MHz. The result is shown in FIG. 6 and FIG. 7.

Example 4

Cloning of Enoyl-CoA Hydratase gene from *Streptomyces* sp. CFMR 7

Initially, genomic DNA was isolated *Streptomyces* sp. CFMR 7 QIAamp DNA Mini Kit The vector with polymer synthase of BP-M-CPF4 with the SwaI restriction site was prepared by repeated experiment [0079] to [0083] by using primers SEQ ID NO:7 and SEQ ID NO:8 to replace SEQ ID NO:5 and SEQ ID NO:6.

To amplify enoyl-CoA hydratase gene from genomic DNA of *Streptomyces* sp. CFMR 7, two specific oligonucleotides, SEQ ID NO:9 and SEQ ID NO:10, were synthesized.

The enoyl-CoA hydratase gene was amplified by PCR using these oligonucleotides as primers and the genomic DNA from *Streptomyces* sp. CFMR 7. The PCR conditions were as follow: 94° C. for 3 min; 30 cycles of 94° C. for 30 s, 57° C. for 30 s, and 72° C. for 2 min; and a final step at 72° C. for 10 min.

The nucleotide sequence of 850 bp SwaI-SwaI from this fragment was determined by the Sanger method.

Example 5

Preparation of *C. necator* Transformant

The SwaI-SwaI enoyl-CoA hydratase gene fragment was inserted into a recombinant vector pBBR1MCS-2 with polymer synthase of BP-M-CPF4 that construction previously, and the resulting recombinant plasmid was transformed into *Cuprividus necator* (DSM 541) (strain deficient in the ability to synthesize polymer) by the conjugation transfer method. The recombinant vector construct at [0099] was also used as the negative control for comparison the effect of enoyl-CoA hydratase.

Firstly, the recombinant plasmids were used to transform *E. coli* S17-1 by the calcium chloride method. The recombinant *E. coli* thus obtained and *C. necator* PHB⁻4 were transconjugated. The recombinant *E. coli* and *C. necator* PHB⁻4 were cultured overnight in 1.5 mL LB medium and nutrient rich medium at 30° C. and the respective culture, each 0.1 mL, were combined and cultured on a shaker at room temperature for 1 hour. The mixture was then incubated without shaking for 30 minutes, and subsequently shaken again for 30 minutes. This microbial mixture was plated on Simmon's citrate agar containing 300 mg/L kanamycin and cultured at 30° C. for 2 days.

Since *C. necator* PHB⁻4 is rendered resistant to kanamycin by transferring the plasmid in the recombinant *E. coli* into it, the colonies grown on the Simmon's citrate agar are a transformant of *C. necator*.

Example 6

Synthesis of Polymer by *C. necator* Transformants

Each of *C. necator* transformants were inoculated into 50 mL mineral medium (4.0 g/L $NaH_2PO_4$, 4.6 g/L $Na_2HPO_4$, 0.45 g/L $K_2SO_4$, 0.54 g/L Urea, 0.39 g/L $MgSO_4$, 0.062 g/L $CaCl_2$ and 1 ml/L of trace elements and incubated in a flask at 30° C. The trace element solution consisted of 15 g/L $FeSO_4 \cdot 7H_2O$, 2.4 g/L $MnSO_4 \cdot H_2O$, 2.4 g/L $ZnSO_4 \cdot 7H_2O$, and 0.48 g/L $CuSO_4 \cdot 5H_2O$ dissolved in 0.1 M hydrochloric acid. 50 mg/L kanamycin was added in the mediums for *C. necator* transformants and the microorganism were cultured for 48 hours.

Each strain of *C. necator* transformants was inoculated into the above mineral medium to which 6 g/L of palm olein (PO) crude palm kernel oil (CPKO) had been added, and each strain was cultured at 30° C. for 48 hours in a 250 mL flask. 50 mg/L kanamycin was added in the mediums for *C. necator* transformants.

The cultures were recovered by centrifugation, washed with distilled water and hexane (in the presence of CPKO) and lyophilized, and the weight of the dried microorganisms was determined. 2 mL sulfuric acid/methanol mixture (15:85) and 2 mL chloroform were added to 15-20 mg of the dried microorganism, and the simple was sealed and heated at 100° C. for 140 minutes whereby the polymer in the microorganisms was decomposed into methylester. 1 mL distilled water was added thereto and vortexed vigorously. It was left and separated into 2 layers, and the lower organic layer was removed and analysed for its components by capillary gas chromatography through a capillary column. The PHA content was determined by gas chromatography (GC) using the Shimadzu GC-2010 system equipped with an SPB-1 column (Supelco, USA). The column temperature was initiated at 70° C. and then increased to 280° C. in continuous steps of 10° C./min. The PHA content and composition were quantified with caprylic acid methyl ester (CME) as an internal standard.

Approximately one gram of lyophilized cell was mixed with 50 mL of chloroform and stirred at room temperature for three days. The mixture was filtered using Whatman No. 1 filter papers to remove cell debris. The resulting clear solution was then added dropwise into vigorously stirring ice-cold methanol to precipitate the PHA polymers. The precipitated polymers were separated from the methanol solution using vacuum filtration and then dried overnight at room temperature. Solvent extraction of PHA from the bacterial cells was usually able to produce the highest purity (95 to 100%) of PHA polymers.

The resulting polymer were used to measure the number average molecular weight ($M_n$) and weight average molecular weight ($M_w$) by gel permeation chromatography (GPC) using Agilent Technologies 1200 Series GPC (USA) equipped with Shodex K806-M and K802 columns (Japan). Chloroform was used as the solvent for the mobile phase with a flow rate of 0.8 mL/min at 40° C. PHA polymers were dissolved in chloroform to a final concentration of approximately 1.0 mg/mL and filtered (PTFE membrane, 0.22 μm) before analysis.

The resulting polymer is confirmed by nuclear magnetic resonance. A total of 25 mg of polymer sample is dissolved in 1 mL of deuterated chloroform ($CDCL_3$). PHA polymers were analyzed by $^1$NMR spectroscopy using a Bruker AVANCE 500 (USA) operating at 500 MHz.

Table 2 shows the biosynthesis of PHA by *C. necator* transformant with and without phaJ$_{Ss}$, from PO and CPKO.

TABLE 2

| Strain | Carbon source | Dry cell weight (g/L) | PHA content (wt %)[a] | Monomer composition (mol %) | | Molecular weight (Da) | | |
|---|---|---|---|---|---|---|---|---|
| | | | | 3HB | 3HHx | $M_n$ (×10$^5$) | $M_w$ (×10$^5$) | $M_w/M_n$ |
| PHB⁻4/pBBR1MCS2_$C_{BP-M-CPF4}$ | PO | 4.9 ± 0.5 | 53 ± 6 | 96 ± 0 | 4 ± 0 | 3.7 ± 0.0 | 9.9 ± 0.0 | 2.7 ± 0.1 |
| PHB⁻4/pBBR1MCS2_$C_{BP-M-CPF4}$ | CPKO | 5.6 ± 0.3 | 58 ± 2 | 93 ± 0 | 7 ± 0 | 3.8 ± 0.1 | 12.3 ± 0.5 | 3.3 ± 0.2 |
| PHB⁻4/pBBRMCS2_$C_{BP-M-CPF4}$_$J_{Ss}$ | PO | 5.0 ± 0.1 | 54 ± 4 | 88 ± 1 | 12 ± 0 | 3.0 ± 0.0 | 8.0 ± 0.1 | 2.7 ± 0.0 |
| PHB⁻4/pBBRMCS2_$C_{BP-M-CPF4}$_$J_{Ss}$ | CPKO | 5.6 ± 0.1 | 62 ± 4 | 82 ± 0 | 18 ± 0 | 3.1 ± 0.0 | 8.9 ± 0.4 | 2.9 ± 0.1 |

3% inoculum from starter cultures (O.D = ~4.5) was transferred into 50 mL MM in 250 mL conical flask and incubated at 30° C., 48 hours, 200 rpm. Data shown were obtained by GC and GPC analysis. The values reported are averages from triplicate cultures ± SDs.
[a]PHA content in freeze-dried cells
3HB, 3-hydroxybutyrate;
3HHx, 3-hydroxyhexanoate Based on the results in Table 2, the transformant with phaJ (PHB⁻4/pBBRMCS2 $C_{BP-M-CPF4}$_$J_{Ss}$) showed higher 3HHx composition as compared to transformant without phaJ (PHB⁻4/pBB1RMCS2_$C_{BP-M-CPF4}$).

In PO, the cell biomass of PHB⁻4/pBBR1MCS2 $C_{BP-M-CPF4}$ was 4.9±0.5 g/L and the polymer content was 53±6% by weight of the microorganism. Accumulation of P(3HB-co-3HHx) copolymer with 4 mol % of 3HHx was observed and the molecular weight (Mw) of the copolymer was 9.9×10$^5$ Da.

In CPKO, the cell biomass of PHB⁻4/pBBR1MCS2 $C_{BP-M-CPF4}$ was 5.6±0.3 g/L and the polymer content was 58±2% by weight of the microorganism. Accumulation of P(3HB-co-3HHx) copolymer with 7 mol % of 3HHx was observed and the molecular weight (Mw) of the copolymer was 12.3×10$^5$ Da.

In PO, the cell biomass of PHB⁻4/pBBRMCS2_ $C_{BP-M-CPF4}$_$J_{Ss}$ was 5.0±0.1 g/L and the polymer content was 54±4% by weight of the microorganism. Accumulation of P(3HB-co-3HHx) copolymer with 12 mol % of 3HHx was observed and the molecular weight (Mw) of the copolymer was 8.0×10$^5$ Da.

In CPKO, the cell biomass of PHB⁻4/pBBRMCS2 $C_{BP-M-CPF4}$ _$J_{Ss}$ was 5.6±0.1 g/L and the polymer content was 62±4% by weight of the microorganism. Accumulation of P(3HB-co-3HHx) copolymer with 18 mol % of 3HHx was observed and the molecular weight (Mw) of the copolymer was 8.9×10$^5$ Da.

The results obtained in Table 2 were confirmed by $^1$H-NMR analysis wherein the structure of the polymers produced were confirmed to be P(3HB-co-3HHx) and the 3HHx monomer compositions varied between 5%, 10%, 13% and 20% for biosynthesis using transformant with or without phaJ (PHB-4/pBBRMCS2 $C_{BP-M-CPF4}$_$J_{Ss}$ or PHB⁻4/pBBR1MCS2_$C_{BP-M-CPF4}$) and PO or CPKO as carbon sources respectively. The results are shown in FIG. 8 and FIG. 9.

FIG. 8 is $^1$NMR analysis of polymers produced using transformant without phaJ (PHB-4/pBBR1MCS2_CBP-M-CPF4) and (a) PO and (b) CPKO as carbon sources. The 3HHx monomer fractions calculated using NMR analysis are (a) 5 mol % and (b) 10 mol % respectively.

FIG. 9 is $^1$NMR analysis of polymers produced using transformant with phaJ (PHB⁻4/pBBRMCS2) $C_{BP-M-CPF4}$_$J_{Ss}$) and (a) PO and (b) CPKO as carbon sources. The 3HHx monomer fractions calculated using NMR analysis are (a) 13 mol % and (b) 20 mol % respectively.

The invention claimed is:

1. A recombinant vector, which is a plasmid or phage, comprising:
an isolated polynucleotide encoding for a polypeptide with polymer synthase activity comprising an amino acid sequence set forth in SEQ ID NO: 1 or an amino acid sequence set forth in SEQ ID NO: 1, wherein only one of amino acids thereof is replaced, deleted or added, and
an isolated polynucleotide encoding for a polypeptide with hydratase activity comprising an amino acid sequence set forth in SEQ ID NO: 3 or an amino acid sequence set forth in SEQ ID NO: 3, wherein only one of amino acids thereof is replaced, deleted or added.

2. The recombinant vector according to claim 1, further comprising:
an isolated polynucleotide encoding for a polypeptide with polymer synthase activity comprising
a nucleotide sequence set forth in SEQ ID NO: 2 or
a nucleotide sequence set forth in SEQ ID NO: 2, wherein only one of nucleotides thereof is replaced, or the complementary sequence thereof, or wherein T is replaced by U; or the complementary sequence thereof,
and
an isolated polynucleotide encoding for a polypeptide with hydratase activity comprising
a nucleotide sequence set forth in SEQ ID NO: 4 or
a nucleotide sequence set forth in SEQ ID NO: 4, wherein only one of nucleotides thereof is replaced, or the complementary sequence thereof, or wherein T is replaced by U; or the complementary sequence thereof.

3. A transformant transformed by the recombinant vector according to claim 1.

4. A process for producing polymer comprising: culturing the transformant according to claim 3 in a medium containing polymerizable materials; and recovering the polymer from the cultured medium.

5. A recombinant strain with genome comprising;
an isolated polynucleotide encoding for a polypeptide with polymer synthase activity comprising an amino acid sequence set forth in SEQ ID NO: 1 or an amino acid sequence set forth in SEQ ID NO: 1, wherein only one of amino acids thereof is replaced, deleted or added, and
an isolated polynucleotide encoding for a polypeptide with hydratase activity comprising an amino acid sequence set forth in SEQ ID NO: 3 or an amino acid sequence set forth in SEQ ID NO: 3, wherein only one of amino acids thereof is replaced, deleted or added.

6. The transformant transformed by the recombinant vector according to claim 3, wherein the recombinant vector, which is a plasmid or phage, comprises:
an isolated polynucleotide encoding for a polypeptide with polymer synthase activity comprising
a nucleotide sequence set forth in SEQ ID NO: 2 or
a nucleotide sequence set forth in SEQ ID NO: 2, wherein only one of nucleotides thereof is replaced, or the complementary sequence thereof, or wherein T is replaced by U; or the complementary sequence thereof, and
an isolated polynucleotide encoding for a polypeptide with hydratase activity comprising
a nucleotide sequence set forth in SEQ ID NO: 4 or
a nucleotide sequence set forth in SEQ ID NO: 4, wherein only one of nucleotides thereof is replaced, or the complementary sequence thereof, or wherein T is replaced by U; or the complementary sequence thereof.

7. The process for producing polymer according to claim 4, wherein
a transformant is transformed by a recombinant vector, which is a plasmid or phage,
the recombinant vector comprises:
an isolated polynucleotide encoding for a polypeptide with polymer synthase activity comprising
a nucleotide sequence set forth in SEQ ID NO: 2 or
a nucleotide sequence set forth in SEQ ID NO: 2, wherein only one of nucleotides thereof is replaced, or the complementary sequence thereof, or wherein T is replaced by U; or the complementary sequence thereof, and
an isolated polynucleotide encoding for a polypeptide with hydratase activity comprising
a nucleotide sequence set forth in SEQ ID NO: 4 or
a nucleotide sequence set forth in SEQ ID NO: 4, wherein only one of nucleotides thereof is replaced, or the complementary sequence thereof, or wherein T is replaced by U; or the complementary sequence thereof.

8. The recombinant strain with genome according to claim 5, comprising:
an isolated polynucleotide encoding for a polypeptide with polymer synthase activity comprising
a nucleotide sequence set forth in SEQ ID NO: 2 or
a nucleotide sequence set forth in SEQ ID NO: 2, wherein only one of nucleotides thereof is replaced, or the complementary sequence thereof, or wherein T is replaced by U; or the complementary sequence thereof, and
an isolated polynucleotide encoding for a polypeptide with hydratase activity comprising
a nucleotide sequence set forth in SEQ ID NO: 4 or
a nucleotide sequence set forth in SEQ ID NO: 4, wherein only one of nucleotides thereof is replaced, or the complementary sequence thereof, or wherein T is replaced by U; or the complementary sequence thereof.

9. A process for producing polymer comprising the following steps of:
culturing the recombinant strain according to claim 5 in a medium containing polymerizable materials; and recovering the polymer from the cultured medium.

10. The process for producing polymer according to claim 9, wherein
a recombinant strain with genome comprises:
an isolated polynucleotide encoding for a polypeptide with polymer synthase activity comprising a nucleotide sequence set forth in SEQ ID NO: 2 or
a nucleotide sequence set forth in SEQ ID NO: 2, wherein only one of nucleotides thereof is replaced, or the complementary sequence thereof, or wherein T is replaced by U; or the complementary sequence thereof, and an isolated polynucleotide encoding for a polypeptide with hydratase activity comprising
a nucleotide sequence set forth in SEQ ID NO: 4 or
a nucleotide sequence set forth in SEQ ID NO: 4, wherein only one of nucleotides thereof is replaced, or the complementary sequence thereof, or wherein T is replaced by U; or the complementary sequence thereof.

11. The process according to claim 4, wherein the polymer is polyhydroxyalkanoate.

12. The process according to claim 7, wherein the polymer is polyhydroxyalkanoate.

13. The process according to claim 9, wherein the polymer is polyhydroxyalkanoate.

14. The process according to claim 10, wherein the polymer is polyhydroxyalkanoate.

15. The process according to claim 4, wherein a carbon source in the step of culturing is crude palm kernel oil.

16. The process according to claim 7, wherein a carbon source in the step of culturing is crude palm kernel oil.

17. The process according to claim 9, wherein a carbon source in the step of culturing is crude palm kernel oil.

18. The process according to claim 10, wherein a carbon source in the step of culturing is crude palm kernel oil.

* * * * *

SEQUENCE LISTING

```
<160> NUMBER OF SEQ ID NOS: 10

<210> SEQ ID NO 1
<211> LENGTH: 544
<212> TYPE: PRT
<213> ORGANISM: Unknown
<220> FEATURE:
<223> OTHER INFORMATION: Uncultured bacterium

<400> SEQUENCE: 1

Met Ala Ser Lys Asp Ser Phe Gly Lys Thr Gly Asp Leu Trp Ser Ser
1               5                   10                  15

Met Phe Asn Trp Met Ser Gly Thr Met Thr Ala Ala Ala Gln Ile Gln
            20                  25                  30

Gln Ala Asn Met Arg Ala Phe Ala Gln Ser Met Glu Leu Ala Thr Ser
        35                  40                  45

Ala Tyr Ala Arg Met Trp Gly Gln Pro Val Glu Gln Val Val Pro Ala
    50                  55                  60
```

```
Asp Arg Arg Phe Lys Asp Glu Ala Trp Thr Glu Asn Met Ala Ala Asp
 65                  70                  75                  80

Leu Leu Lys Gln Ser Tyr Leu Ile Thr Ser Gln Leu Met Glu Ile Ala
                 85                  90                  95

Asp Gly Trp Gln Ala Ile Asp Pro Asp Leu His Glu Arg Thr Arg Phe
            100                 105                 110

Trp Thr Gln Gln Leu Val Asp Ala Thr Ser Pro Ala Asn Phe Ala Met
        115                 120                 125

Thr Asn Pro Val Val Met Gln Glu Ile Ala Arg Thr Gly Gly Met Asn
    130                 135                 140

Leu Ile Gln Gly Ala Gln Asn Leu Leu Lys Asp Ala Gln Ser Gly Arg
145                 150                 155                 160

Leu Thr Gln Val Pro Glu Asp Ala Phe Glu Val Gly Lys Asp Leu Ala
                165                 170                 175

Ile Thr Pro Gly Lys Val Val Tyr Arg Asn Arg Leu Glu Leu Ile Gln
            180                 185                 190

Tyr Thr Pro Ala Thr Glu Thr Val His Glu Ile Pro Ile Leu Val Val
        195                 200                 205

Pro Pro Trp Ile Asn Lys Tyr Tyr Val Met Asp Met Gln Pro Glu Asn
    210                 215                 220

Ser Leu Phe Lys Tyr Leu Val Asp Ala Gly Phe Leu Phe Thr Ile Ser
225                 230                 235                 240

Trp Lys Asn Pro Asp Glu Thr Val Leu Asp Leu Glu Trp Asp Asp Tyr
                245                 250                 255

Leu Asp Leu Gly Thr Leu Glu Ala Leu Arg Met Val Lys Glu Ile Met
            260                 265                 270

Gly Val Glu Gln Val Asn Leu Val Gly Tyr Cys Leu Gly Ile Ile Ser
        275                 280                 285

Gln Val Thr Leu Ala Tyr Leu Ala Ala Thr Gly Asp Asp Ala Gln Ile
    290                 295                 300

Asn Ser Ala Thr Tyr Phe Thr Thr His Gln Asp Phe Ser Asp Ala Gly
305                 310                 315                 320

Glu Ile Ser Val Phe Ile Ser Arg Leu Asp Val Met Phe Leu Glu Met
                325                 330                 335

Lys Ile Ser Gly Gly Tyr Leu Asp Gly Arg Asn Leu Ala Ala Thr Phe
            340                 345                 350

Asn Met Leu Arg Ala Asn Asp Leu Leu Trp Asn Tyr Val Val His Asn
        355                 360                 365

Tyr Leu Leu Gly Gln Glu Pro Ala Ser Phe Asp Leu Leu Tyr Trp Asn
370                 375                 380

Asn Asp Gly Thr Arg Val Pro Gly Lys Val His Ser Phe Leu Leu Arg
385                 390                 395                 400

Glu Phe Phe Leu Asp Asn Lys Leu Lys Glu Pro Glu Gly Ile Gln Val
                405                 410                 415

Lys Gly Val Gly Ile Asp Leu Gly Lys Ile Thr Thr Pro Thr Val Val
            420                 425                 430

Thr Ala Asp Arg Asp His Ile Val Pro Trp Arg Gly Ala Phe Leu Val
        435                 440                 445

Arg Gln Leu Gln Ser Gly Pro Val Arg Phe Ile Leu Ser Gly Gly Gly
                455                 460

His Ile Ala Gly Val Ile Ser Pro Pro Thr Lys Asn Arg Gly Phe Trp
465                 470                 475                 480

Ile Asn Glu Glu Glu Lys Asp Asp Ala Asp Ala Trp Leu Ala Gly Ala
```

485                 490                 495
Thr Lys His Asp Gly Ser Trp Trp Val Asp Trp Ile Pro Trp Leu Glu
                500                 505                 510

Glu Arg Ser Gly Arg Arg Val Lys Pro Pro Thr Ala Ala Gly Ser Asp
                515                 520                 525

Glu Phe Lys Pro Leu Met Asp Ala Pro Gly Thr Tyr Val Leu Glu Lys
        530                 535                 540

<210> SEQ ID NO 2
<211> LENGTH: 1656
<212> TYPE: DNA
<213> ORGANISM: Unknown
<220> FEATURE:
<223> OTHER INFORMATION: Uncultured bacterium

<400> SEQUENCE: 2

```
atggcgtcaa aggatagctt cgggaaaaca ggtgatttgt ggtcatcgat gttcaactgg      60
atgagcggga cgatgacggc cgcggcacag attcagcagg ctaatatgcg ggccttcgcc     120
caaagcatgg aactggcaac cagcgcctat gccaggatgt ggggtcagcc ggtcgaacag     180
gtcgtgccgg ccgatcgacg cttcaaggat gaggcctgga cggaaaacat ggccgccgat     240
ttgctcaaac agagctacct gatcaccagt cagtggctaa tggaaatcgc cgatggttgg     300
caggctatcg atcccgatct gcacgaacgg acccgcttct ggacacagca actcgtcgac     360
gccaccagcc cggctaactt cgccatgacc aacccggtgg tgatgcaaga gatagcccgc     420
actggcggca tgaacctgat ccagggggcg cagaatctat tgaaggatgc ccaaagtggc     480
cggctaaccc aagttcctga ggatgccttt gaggtaggta aggacctggc gatcacgccg     540
ggcaaggtcg tatatcgcaa ccgcctgatt gagttgatcc agtacacgcc ggccacagag     600
acggtccatg aaatccccat cttggtcgtg ccgccatgga tcaataagta ctacgtgatg     660
gacatgcagc cggagaattc gctgttcaag tacctggtgg atgccggctt caccctgttc     720
accatcagct ggaaaaaccc tgatgaaaca gttcttgacc tggaatggga cgactatctg     780
gatctgggca cgctggaagc gctgcgaatg gtcaaggaaa tcatgggtgt cgagcaggtg     840
aacctggtcg gctactgtct aggcgggatc atctcccagg taactttggc ctatctggcg     900
gccactggag acgacgcgca gataaacagc gcgacctatt tcaccaccca ccaggatttc     960
agcgatgcgg cgagatctc ggtcttcatc agccggctgg acgtgatgtt cctggaatgg    1020
ttgatgaaga tcagcggcgg ctacctggat ggccggaacc tggcggctac cttcaacatg    1080
ctgcgggcca atgacctgct atggaattac gtggtccaca attatctctt gggccaggaa    1140
ccggcgtcct ttgatctact ctactggaat aatgacggca ccagggtacc gggcaaggtg    1200
cattcattcc tgctgcgcga attcttcctg gataacaaac tgaaggagcc cgagggtatt    1260
caggtgaagg gcgtgggcat tgacctcggt aaaatcacaa cgccaaccta tgtggtgacg    1320
gccgaccggg atcacatcgt gccctggcgg ggcgcattct tggtgcgcca gttgcagagc    1380
gggccggtgc gcttcatctt gagcggcggc ggacatatcg ccggggtcat tagcccaccc    1440
actaagaacc gcggcttttg gatcaacgaa gaagagaagg atgatgctga tgcctggctg    1500
gccggagcga ccaagcatga cggtagttgg tgggtagatt ggattccatg gctcgaggag    1560
cgctcgggaa gaagggtgaa gccaccgacg gccgccggca gcgacgagtt caaacccctc    1620
atggacgcgc caggcacgta cgttttggag aagtag                               1656
```

<210> SEQ ID NO 3

<211> LENGTH: 285
<212> TYPE: PRT
<213> ORGANISM: Streptomyces sp.

<400> SEQUENCE: 3

Met Pro Ile Asp Ala Arg Ala Ala Leu Ala Ala Pro Arg Arg Ala
1               5                   10                  15

Glu Ile Ala Trp Asn His Lys Asp Val Gln Leu Tyr His Leu Gly Leu
                20                  25                  30

Gly Ala Gly Ile Pro Ala Thr Asp Pro Asp Glu Leu Arg Tyr Thr Leu
                35                  40                  45

Glu Ser Arg Leu Gln Val Leu Pro Ser Phe Ala Thr Val Ala Gly Ala
    50                  55                  60

Gly Thr Ala Ala Phe Gly Met Gly Ala Asp Gly Ile Asp Val Asp
65                  70                  75                  80

Leu Ala Ala Val Leu His Gly Gln Ser Val Arg Val His Arg Pro
                85                  90                  95

Ile Pro Val Thr Gly Arg Ala Val Gln Thr Ser Lys Val Ala Ala Val
                100                 105                 110

Tyr Asp Lys Gly Lys Ala Ala Val Ile Val Leu Arg Thr Glu Ala His
                115                 120                 125

Asp Asp Glu Gly Pro Leu Trp Thr Asn Asp Ala Gln Ile Phe Val Arg
    130                 135                 140

Gly Glu Gly Gly Phe Gly Gly Glu Arg Gly Pro Ala Asp Arg Leu Ala
145                 150                 155                 160

Leu Pro Asp Arg Ala Pro Asp Arg Thr Ala Glu Arg Pro Ile Arg Glu
                165                 170                 175

Asp Gln Ala Leu Leu Tyr Arg Leu Ser Gly Asp Trp Asn Pro Leu His
                180                 185                 190

Ala Asp Pro Ala Phe Ala Lys Leu Ala Gly Phe Asp Arg Pro Ile Leu
            195                 200                 205

His Gly Leu Cys Thr Tyr Gly Met Val Leu Lys Ala Val Thr Asp Thr
    210                 215                 220

Leu Leu Asp Gly Asp Val Ser Arg Ile Ala Ala Tyr Arg Thr Arg Phe
225                 230                 235                 240

Ala Gly Val Val Phe Pro Gly Glu Thr Leu Arg Ile Arg Met Trp Gln
                245                 250                 255

Val Gly Asp Gly Arg Val Gln Val Ala Val Thr Ala Ala Gly Arg Asp
                260                 265                 270

Asp Ala Pro Val Leu Ala Asp Thr Leu Val Glu His Ser
        275                 280                 285

<210> SEQ ID NO 4
<211> LENGTH: 855
<212> TYPE: DNA
<213> ORGANISM: Streptomyces sp.

<400> SEQUENCE: 4
atgcccatcg atgccgagc ggccctcgcc gcagccccc gccgagccga gatcgcctgg      60
aaccacaagg acgtccagct ctaccacctg ggcctcggcg cggggatccc cgccaccgac     120
ccggacgagc tgcgctacac cctggagtcc cggctccagg tgctgccgag cttcgccacc     180
gtcgcgggcg ccgggacggc cgccttcggc gggatgggcg cggacgggat cgacgtggac     240
ctcgccgccg tcctgcacgg cggccagtcc gtccgcgtcc accgcccgat ccccgtcacc     300
ggccgggccg tgcagacctc gaaggtcgcg gccgtgtacg acaagggcaa ggccgccgtc     360

```
atcgtgctcc gtaccgaggc gcacgacgat gaggggccgc tctggaccaa cgacgcgcag    420
atcttcgtac ggggagaggg cggattcggc ggcgagcgcg ggcccgccga ccgcctcgcc    480
ctgcccgacc gggcccccga ccgcaccgcc gaacgcccga tccgcgagga ccaggcgctg    540
ctctaccgcc tctccgggga ctggaacccg ctccacgccg acccggcctt cgccaagctc    600
gccggcttcg accggccgat cctgcacgga ctgtgcacgt acggcatggt cctcaaggcc    660
gtcaccgaca ccctgctgga cggcgacgtc tcccggatcg ccgcctaccg cacccgcttc    720
gccggagtgg tcttccccgg cgagaccctc cgcatccgga tgtggcaggt cggggacggg    780
cgcgtccagg tggccgtgac cgccgccgga cgggacgacg ccccggtcct cgcggacacg    840
ctcgtcgaac actcc                                                    855
```

```
<210> SEQ ID NO 5
<211> LENGTH: 46
<212> TYPE: DNA
<213> ORGANISM: Unknown
<220> FEATURE:
<223> OTHER INFORMATION: Uncultured bacterium

<400> SEQUENCE: 5
agtaagcttc aaaggaggga aagtatggcg tcaaaggata gcttcg               46

<210> SEQ ID NO 6
<211> LENGTH: 32
<212> TYPE: DNA
<213> ORGANISM: Unknown
<220> FEATURE:
<223> OTHER INFORMATION: Uncultured bacterium

<400> SEQUENCE: 6
attgggccct tcgctcatca gtctacttct cc                              32

<210> SEQ ID NO 7
<211> LENGTH: 44
<212> TYPE: DNA
<213> ORGANISM: Streptomyces sp.

<400> SEQUENCE: 7
agtaagcttc aaaggaggga aagtatggcg tcaaaggata gctt                 44

<210> SEQ ID NO 8
<211> LENGTH: 37
<212> TYPE: DNA
<213> ORGANISM: Streptomyces sp.

<400> SEQUENCE: 8
tatgggccca tttaaatcta cttctccaaa acgtacg                         37

<210> SEQ ID NO 9
<211> LENGTH: 43
<212> TYPE: DNA
<213> ORGANISM: Streptomyces sp.

<400> SEQUENCE: 9
atcatttaaa taggagggaa agtatgccca tcgatgcccg agc                  43

<210> SEQ ID NO 10
<211> LENGTH: 35
<212> TYPE: DNA
<213> ORGANISM: Streptomyces sp.
```

```
<400> SEQUENCE: 10
agcatttaaa ttcaggagtg ttcgacgagc gtgtc                                  35
```